(12) United States Patent
Teshima et al.

(10) Patent No.: US 8,207,201 B2
(45) Date of Patent: Jun. 26, 2012

(54) AGENT FOR PROPHYLAXIS OR TREATMENT OF ALCOHOL DEPENDENCE OR DRUG DEPENDENCE

(75) Inventors: Koji Teshima, Osaka (JP); Roberto Ciccocioppo, Camerino (IT); Maurizio Massi, Camerino (IT)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 12/311,861

(22) PCT Filed: Oct. 16, 2007

(86) PCT No.: PCT/JP2007/070502
§ 371 (c)(1),
(2), (4) Date: Jul. 15, 2009

(87) PCT Pub. No.: WO2008/050698
PCT Pub. Date: May 2, 2008

(65) Prior Publication Data
US 2010/0069382 A1 Mar. 18, 2010

(30) Foreign Application Priority Data
Oct. 16, 2006 (EP) ..................... 06122336

(51) Int. Cl.
*A61K 31/454* (2006.01)
(52) U.S. Cl. ........................ 514/322; 546/199
(58) Field of Classification Search .................. None
See application file for complete search history.

(56) References Cited

U.S. PATENT DOCUMENTS

| 6,423,725 | B1 | 7/2002 | Ito et al. | |
|---|---|---|---|---|
| 2005/0070528 | A1 | 3/2005 | Den Hartog et al. | |
| 2005/0119308 | A1 | 6/2005 | Teshima et al. | |
| 2011/0178128 | A1* | 7/2011 | Sekiguchi et al. | 514/322 |

FOREIGN PATENT DOCUMENTS

| EP | 1491212 | 12/2004 |
|---|---|---|
| WO | 99/36421 | 7/1999 |
| WO | 03/082333 | 10/2003 |
| WO | 2005/028466 | 3/2005 |
| WO | WO 2006025267 A1 * | 3/2006 |

OTHER PUBLICATIONS

Bignan et al., Expert Opinion Thera. Patents 15(4), pp. 357-388 (2005).*
International Search Report issued May 6, 2008 in the International (PCT) Application PCT/JP2007/070502 of which the present application is the U.S. National Stage.
Chiou et al., *Nociceptin/Orphanin FQ Peptide Receptors: Pharmacology and Clinical Implications*, Current Drug Targets, vol. 8, pp. 117-135 (2007).
Teshima et al., *Nonphotic Entrainment of the Circadian Body Temperature Rhythm by the Selective ORL1 Receptor Agonist W-212393 in Rats*, British Journal Pharmacology, vol. 146, pp. 33-40 (2005).
Ciccocioppo et al., *Attenuation of Ethanol Self-administration and of Conditioned Reinstatement of Alchol-seeking Behavior by the Antiopioid Peptide Nociceptin/Orphanin FQ in Alcohol-preferring Rats*, Psychopharmacology, vol. 172, pp. 170-178 (2004).
Zhao et al., *Orphanin FQ/Nociceptin Blocks Methamphetamine Place Preference in Rats*, NeuroReport vol. 14, No. 18, pp. 2383-2385 (2003).
Bunzow et al. *Molecular Cloning and Tissue Distribution of a Putative Member of the Rat Opioid Receptor Gene Family that is not a µ, δ or κ Opioid Receptor Type*, FEBS Letters, vol. 347, pp. 284-288 (1994).
Mollereau et al., *ORL1, a Novel Member of the Opioid Receptor Family Cloning, Functional Expression and Localization*, FEBS Letters, vol. 341, pp. 33-38 (1994).
Meunier, *Nociceptin/Orphanin FQ and the Opioid Receptor-like ORL1 Receptor*, European Journal Pharmacology vol. 340, pp. 1-15 (1997).
Mogil et al., *The Molecular and Behavioral Pharmacology of the Orphanin FQ/Nociceptin Peptide and Receptor Family*, Pharmacological Review, vol. 53, No. 3, pp. 381-415 (2001).
Meunier, et al., *Isolation and Structure of the Endogenous Agonist of Opioid Receptor-like ORL1 Receptor*, Nature, vol. 377, pp. 532-535 (1995).
Reinscheid et al., *Orphanin FQ: A Neuropeptide that Activates an Opioidlike G Protein-Coupled Receptor*, Science, vol. 270, pp. 792-794 (1995).
Calo et al., *Pharmacology of Nociceptin and its Receptor: a Novel Therapeutif Target*, British Journal of Pharmacology, vol. 129, pp. 1261-1283 (2000).
Ciccocioppo et al., *Effect of Nociceptin on Alcohol Intake in Alcohol-preferring Rats*, Psychopharmacology, vol. 141, pp. 220-224 (1999).
Martin-Fardon et al., *Nociceptin Prevents Stress-Induced Ethanol—but not Cocaine-seeking Behavior in Rats*, NeuroReport, vol. 11, No. 9, pp. 1939-1943 (2000).
Sakoori et al., *Central Administration of Nociceptin/Orphanin FQ Blocks the Acquisition of Conditioned Place Preference to Morphine and Cocaine, but not Conditioned Place Aversion to Naloxone in Mice*, Psychopharmacology, vol. 172, pp. 129-136 (2004).

(Continued)

*Primary Examiner* — Kamal Saeed
*Assistant Examiner* — Nyeemah A Grazier
(74) *Attorney, Agent, or Firm* — Wenderoth, Lind & Ponack, L.L.P.

(57) ABSTRACT

The present invention provides an agent for the prophylaxis or treatment of substance abuse and dependence, which contains a compound of the formula (I) represented by (R)-2-{3-[1-(acenaphthen-1-yl)piperidin-4-yl]-2,3-dihydro-2-oxo-benzimidazol-1-yl}-N-methylacetamide, or a pharmaceutically acceptable salt thereof as an active ingredient.

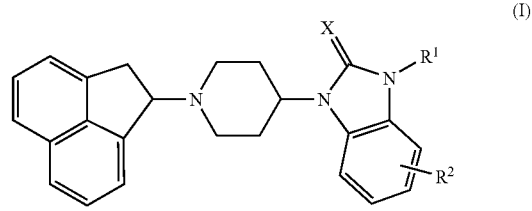

(I)

3 Claims, 4 Drawing Sheets

OTHER PUBLICATIONS

Kakko et al. *1-year Retention and Social Function after Buprenorphine-assisted Relapse Prevention Treatment for Heroin Dependence in Sweden: a Randomised, Placebo-controlled Trial*, The Lancet, vol. 361, pp. 662-668 (2003).

Ling et al. *Buprenorphine Maintenance Treatment of Opiate Dependence: a Multicenter, Randomized Clinical Trial*, Addiction, vol. 93, No. 4, pp. 475-486 (1998).

Montoya et al., *Randomized Trial of Buprenorphine for Treatment of Concurrent Opiate and Cocaine Dependence*, Clinical Pharmacology and Therapeutics, vol. 75, No. 1, pp. 34-48 (2004).

Schottenfeld et al., *Buprenorphine: Dose-related Effects on Cocaine and Opioid Use in Cocaine-Abusing Opioid-dependent Humans*, Biol. Psychiatry, vol. 34, pp. 66-74 (1993).

Ciccocioppo et al., *Buprenorphine Reduces Alcohol Drinking Through Activation of the Nociceptin/Orphanin FQ-NOP Receptor System*, Biol. Psychiatry, vol. 61, pp. 4-12 (2007).

Economidou et al., *Effect of Novel Nociceptin/Orphanin FQ-NQP Receptor Ligands on Ethanol Drinking in Alcohol-Preferring msP Rats*, Peptides, vol. 27, pp. 3299-3306 (2006).

Kuzmin et al. *The Nociceptin/Orphanin FQ Receptor Agonist Ro 64-6198 Reduces Alcohol Self-Adminstration and Prevents Relapse-Like Alcohol Drinking*, Neuropsychopharmacology, vol. 32, pp. 902-910 (2007).

\* cited by examiner

Compound A or vehicle treatment

| Pre-conditioning | Conditioning | | | | | | Test |
|---|---|---|---|---|---|---|---|
| Day 1 | Day 2 | Day 3 | Day 4 | Day 5 | Day 6 | Day 7 | Day 8 | Day 9 |

AGENT FOR PROPHYLAXIS OR TREATMENT OF ALCOHOL DEPENDENCE OR DRUG DEPENDENCE

TECHNICAL FIELD

The present invention relates to an agent for the prophylaxis or treatment of substance abuse and dependence, which comprises an ORL-1 receptor agonist as an active ingredient.

BACKGROUND ART

After cloning of δ, κ, μ receptors, the opioid receptor-like 1 (ORL-1) receptor was cloned as the forth member of the opioid receptor family in 1994, (FEBS Lett. 347, 284-288, 1994, FEBS Lett. 341, 33-38, 1994). Although ORL-1 receptor has about 60% of homology to other opioid receptors, it is clearly different from other opioid receptors, because non-selective opioid receptor antagonist, naloxone, does not bind to the ORL-1 receptor (FEBS Lett. 341, 33-38, 1994). While the ORL-1 receptor is expressed in the periphery organs such as intestine, spleen and so on, it is also widely expressed in the central nervous system, especially in the cortex, hippocampus, hypothalamus, amygdala and spinal cord (Eur. J. Pharmacol. 340, 1-15, 1997, Pharmacol. Rev. 53, 381-415, 2001).

In 1995, the endogenous ligand for the ORL-1 receptor was identified by two different research groups in France and Switzerland at the same time, and named as nociceptin (Nature 377, 532-535, 1995) and orphanin FQ (Science 270, 792-794, 1995), respectively. Nociceptin is a 17-amino acid peptide and 30 plays an important role in the function of central nervous system such as learning, memory, anxiety and stress (Br. J. Pharmacol. 129, 1261-1283, 2000).

Substance abuse and dependence involves any of following classes of substances: alcohol, amphetamine, methamphetamine, cannabis (including marijuana, hashish), cocaine, hallucinogens (including LSD, mescaline, MDMA), nicotine, opioids (including morphine, heroin, codeine, methadone), phencyclidine, ketamine, barbiturates, benzodiazepines (including diazepam, triazolam), inhalants(including toluene, paint thinner).

It is known that the nociceptin, an endogenous agonist for the ORL-1 receptor, is effective in alcohol dependence (Ciccocioppo et al., Psychopharmacology (Berl). 141, 220-224, 1999; Ciccocioppo et al., Psychopharmacology (Berl) 172, 170-178, 2004; Martin-Fardon et al., NeuroReport. 11, 1939-1943, 2000), morphine or cocaine dependence (Sakoori et al., Psychopharmacology (Berl) 172, 129-136, 2004), methamphetamine dependence (Zhao et al., NeuroReport. 14, 2383-2385, 2003).

Furthermore, buprenorphine, a partial agonist at μ opioid and ORL-1 receptors, has been used in clinical for treatment of heroin dependence in numerous countries including the United States, Australia, Sweden and France (Kakko et al., Lancet 361, 662-668, 2003; Ling et al., Addiction 93, 475-486, 1998). Buprenorphine also reduces cocaine use by dually opiate-dependent and cocaine-dependent outpatients (Montoya et al., Clin Pharmacol Ther 75, 34-48, 2004; Schottenfeld et al., Biol Psychiatry 34, 66-74, 1993). More recently, evidence has accumulated in support of its efficacy for treatment of alcohol abuse and dependence (Ciccocioppo et al., Biol Psychiatry 61, 4-12, 2007).

Therefore a small molecule ORL-1 receptor agonist is expected to be effective in the prophylaxis or treatment of for substance abuse and dependence. However, first synthesized ORL-1 receptor agonist Ro64-6198 failed to decrease alcohol drinking, rather increase it at high dose (Economidou et al., Peptides 27, 3299-3306, 2006). This effect probably induced by its residual agonistic activity at μ opioid receptors.

The compound of represented by the formula (I) mentioned in the below, for example, (R)-2-{3-[1-(acenaphthen-1-yl)piperidin-4-yl]-2,3-dihydro-2-oxo-benzimidazol-1-yl}-N-methylacetamide (same as 2-{3-[1-((1R)-acenaphthen-1-yl)piperidin-4-yl]-2,3-dihydro-2-oxo-benzimidazol-1-yl}-N-methylacetamide), is another agonist which possesses highly selective affinity for ORL-1 receptors (WO03/082333).

DISCLOSURE OF THE INVENTION

The present inventors have evaluated the effectiveness of the ORL-1 receptor agonist, (R)-2-{3-(1-(acenaphten-1-yl)piperidin-4-yl)-2,3-dihydro-2-oxo-benzimidazol-1-yl}-N-methylacetamide, in alcohol dependence rat model and found that this compound significantly inhibits alcohol intake of the rat model. Further studies have resulted in the completion of the present invention.

Accordingly, the present invention provides the following.
1. An agent for the prophylaxis or treatment of substance abuse and dependence, which comprises a compound represented by the formula (I)

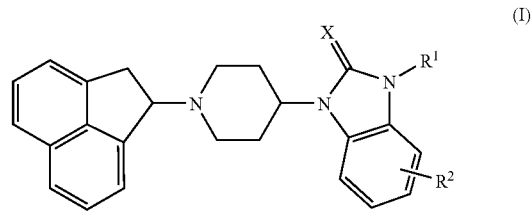

(I)

wherein
R$^1$ is
(1) hydrogen,
(2) lower alkyl,
(3) lower alkenyl,
(4) —C(O)-lower alkyl,
(5) —C(O)O-lower alkyl,
(6) —C(O)-phenyl (the phenyl group may be substituted with lower alkyl, halogen, lower alkoxy, phenoxy or benzyloxy),
(7) lower alkyl-carboxyl,
(8) lower alkyl-C(O)-phenyl (the phenyl group may be substituted with lower alkyl, halogen, lower alkoxy, phenoxy or benzyloxy),
(9) lower alkyl-C(O)O-lower
(10) lower alkenyl-C(O)O-lower alkyl,
(11) lower alkyl-O-lower alkyl,
(12) lower alkyl-C(O)NR$^3$R$^4$,
(13) —S(O)$_2$-lower alkyl,
(14) —S(O)$_2$-phenyl (the phenyl group may be substituted with lower alkyl, halogen, lower alkoxy, phenoxy or benzyloxy),
(15) lower alkyl-S-lower alkyl,
(16) lower alkyl-S(O)-lower alkyl,
(17) lower alkyl-S(O)$_2$-lower alkyl,
(18) lower alkyl-S(O)$_2$NR$^3$R$^4$,
(19) phenyl (the phenyl group may be substituted with lower alkyl, halogen, lower alkoxy, phenoxy or benzyloxy), or
(20) benzyl (the phenyl group may be substituted with lower alkyl, halogen, lower alkoxy, phenoxy or benzyloxy), R² is hydrogen, lower alkyl, halogen, lower alkoxy, phenoxy, benzyloxy, trifluoromethyl, nitro, amino or cyano, R³ and R⁴
may be the same or different, and each is hydrogen, lower alkyl or lower alkenyl, or R³ and R⁴ may bind with an adjacent nitrogen atom to form a saturated nitrogen-containing hetero ring (the hetero ring may be substituted with lower alkyl, halogen, lower alkoxy, phenoxy or benzyloxy), and X is O or S.).

or a pharmaceutically acceptable salt thereof as an active ingredient.

2. The agent of above-mentioned 1, wherein the substance abuse and dependence is abuse of and dependence on alcohol, amphetamine, methamphetamine, cannabis, cocaine, hallucinogens, nicotine, opioids, phencyclidine, ketamine, barbiturates, benzodiazepines or inhalants.

3. The agent of above-mentioned 1, wherein the substance abuse and dependence is abuse of and dependence on alcohol.

4. The agent of above-mentioned 1, wherein the compound represented by the formula (I) or a pharmaceutically acceptable salt thereof is a compound selected from

[1] (RS)-1-[1-(acenaphthen-1-yl)piperidin-4-yl]-1,3-dihydro-2H-benzimidazol-2-one,
[2] (RS)-1-[1-(acenaphthen-1-yl)piperidin-4-yl]-1,3-dihydro-5-fluoro-2H-benzimidazol-2-one,
[3] (RS)-1-[1-(acenaphthen-1-yl)piperidin-4-yl]-1,3-dihydro-6-fluoro-2H-benzimidazol-2-one,
[4] ethyl(RS)-2-{3-[1-(acenaphthen-1-yl)piperidin-4-yl]-2,3-dihydro-2-oxo-benzimidazol-1-yl}acetate,
[5] (RS)-2-{3-[1-(acenaphthen-1-yl)piperidin-4-yl]-2,3-dihydro-2-oxo-benzimidazol-1-yl}acetic acid,
[6] (RS)-1-[1-(acenaphthen-1-yl)piperidin-4-yl]-3-(2-oxo-2-piperazin-1-ylethyl)-1,3-dihydro-2H-benzimidazol-2-one dihydrochloride,
[7] (RS)-1-[1-(acenaphthen-1-yl)piperidin-4-yl]-3-[2-(4-methylpiperazin-1-yl)-2-oxoethyl]-1,3-dihydro-2H-benzimidazol-2-one dihydrochloride,
[8] (RS)-1-[1-(acenaphthen-1-yl)piperidin-4-yl]-3-(2-morpholin-4-yl-2-oxoethyl)-1,3-dihydro-2H-benzimidazol-2-one hydrochloride,
[9] (RS)-1-[1-(acenaphthen-1-yl)piperidin-4-yl]-1,3-dihydro-2H-benzimidazole-2-thione,
[10] (RS)-1-[1-(acenaphthen-1-yl)piperidin-4-yl]-1,3-dihydro-3-methyl-2H-benzimidazole-2-thione,
[11] (R)-1-[1-(acenaphthen-1-yl)piperidin-4-yl]-1,3-dihydro-2H-benzimidazol-2-one,
[12] (S)-1-[1-(acenaphthen-1-yl)piperidin-4-yl]-1,3-dihydro-2H-benzimidazol-2-one,
[13] (R)-3-acetyl-1-[1-(acenaphthen-1-yl)piperidin-4-yl]-1,3-dihydro-2H-benzimidazol-2-one,
[14] (R)-1-[1-(acenaphthen-1-yl)piperidin-4-yl]-3-methanesulfonyl-1,3-dihydro-2H-benzimidazol-2-one,
[15] ethyl (R)-2-{3-[1-(acenaphthen-1-yl)piperidin-4-yl]-2,3-dihydro-2-oxo-benzimidazol-1-yl}acetate,
[16] (R)-2-{3-[1-(acenaphthen-1-yl)piperidin-4-yl]-2,3-dihydro-2-oxo-benzimidazol-1-yl}acetic acid,
[17] (R)-1-[1-(acenaphthen-1-yl)piperidin-4-yl]-3-(2-oxo-2-piperazin-1-ylethyl)-1,3-dihydro-2H-benzimidazol-2-one dihydrochloride,
[18] (R)-2-{3-[1-(acenaphthen-1-yl)piperidin-4-yl]-2,3-dihydro-2-oxo-benzimidazol-1-yl}-N-methylacetamide,
[19] (R)-2-{3-[1-(acenaphthen-1-yl)piperidin-4-yl]-2,3-dihydro-2-oxo-benzimidazol-1-yl}-N,N-dimethylacetamide, and
[20] (R)-2-{3-[1-(acenaphthen-1-yl)piperidin-4-yl]-2,3-dihydro-2-oxo-benzimidazol-1-yl}acetamide.

5. The agent of above-mentioned 1, wherein the compound represented by the formula (I) is (R)-2-{3-[1-(acenaphthen-1-yl)piperidin-4-yl]-2,3-dihydro-2-oxo-benzimidazol-1-yl}-N-methylacetamide.

The present invention further provides the following.

6. Use of a compound represented by the formula (I)

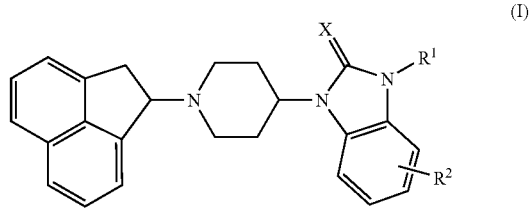

(I)

wherein R¹, R² and X are the same as defined above, or a pharmaceutically acceptable salt thereof for the production of an agent for the prophylaxis or treatment of substance abuse and dependence.

7. A method for the prophylaxis or treatment of substances abuse and dependence, which comprises administering an effective amount of compound represented by the formula (I)

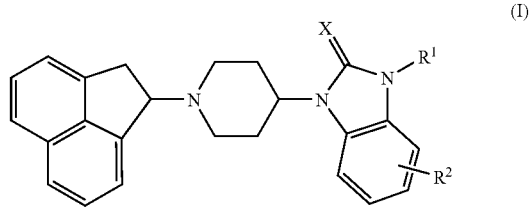

(I)

wherein R¹, R² and X are the same as defined above, or a pharmaceutically acceptable salt thereof.

In the present specification, lower alkyl means alkyl having 1 to 6 carbon atoms such as methyl, ethyl, propyl, isopropyl, butyl, isobutyl, sec-butyl, tert-butyl, pentyl, isopentyl or hexyl, lower alkenyl means alkenyl having 2 to 6 carbon atoms such as vinyl, 1-propenyl, 2-propenyl, isopropenyl, 1-butenyl, 2-butenyl or 3-butenyl, lower alkoxy means alkoxy having 1 to 6 carbon atoms such as methoxy, ethoxy, propoxy, isopropoxy, butoxy, isobutoxy, sec-butoxy, tert-butoxy, pentyloxy, isopentyloxy or hexyloxy, and halogen means chlorine, fluorine, iodine or bromine.

Effect of the Invention

Figure 1:
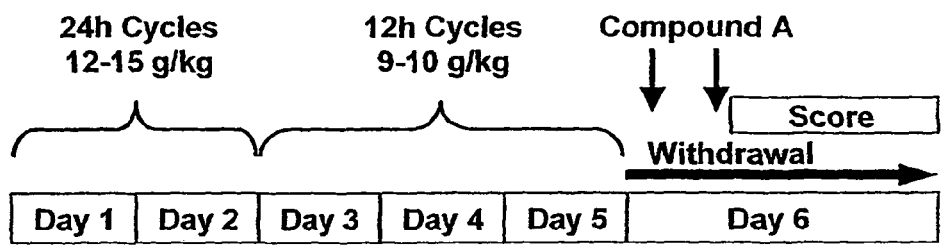
FIG. 1 shows a test protocol of alcohol withdrawal.

The present invention provides an agent effective in the prophylaxis or treatment of substance abuse and dependence. More particularly, the present invention provides a pharmaceutical agent useful for the prophylaxis or treatment of excessive alcohol intake, alcohol dependence and the like, as well as a pharmaceutical agent useful for the prophylaxis or treatment of other substance abuse of and dependence on amphetamine, methamphetamine, cannabis, cocaine, hallucinogens, nicotine, opioids, phencyclidine, ketamine, barbiturates, benzodiazepines, inhalants and the like.

BEST MODE FOR EMBODYING THE INVENTION

The present invention is explained in detail in the following.

In the present invention, the "substance abuse and dependence" includes abuse of and dependence on alcohol, amphetamine, methamphetamine, cannabis (including marijuana, hashish), cocaine, hallucinogens (including LSD, mescaline, MDMA), nicotine, opioids (including morphine, heroin, codeine, methadone), phencyclidine, ketamine, barbiturates, benzodiazepines (including diazepam, triazolam), inhalants (including toluene, paint thinner) and the like.

The agent for the prophylaxis or treatment of substance abuse and dependence of the present invention (hereinafter sometimes to be referred to as the pharmaceutical agent*of the present invention) contains a compound represented by the above formula (I) or a pharmaceutically acceptable salt thereof as an active ingredient.

In the compound represented by the formula (I), preferable $R^1$ is —C(O)-lower alkyl, lower alkyl-C(O)$NR^3R^4$ (either $R^3$ or $R^4$ is hydrogen and the other is lower alkyl) or lower alkyl-C(O)$NR^3R^4$ wherein $R^3$ and $R^4$ bind with an adjacent nitrogen atom to form a saturated nitrogen-containing hetero ring (the hetero ring may be substituted with lower alkyl, halogen, lower alkoxy, phenoxy or benzyloxy). Preferable $R^2$ is hydrogen, and preferable X is O.

The following compounds included in the formula (I) are more preferable in the present invention.
(RS)-1-[1-(acenaphthen-1-yl)piperidin-4-yl]-1,3-dihydro-2H-benzimidazol-2-one,
(R)-1-[1-(acenaphthen-1-yl)piperidin-4-yl]-1,3-dihydro-2H-benzimidazol-2-one,
(S)-1-[1-(acenaphthen-1-yl)piperidin-4-yl]-1,3-dihydro-2H-benzimidazol-2-one,
(R)-3-acetyl-1-[1-(acenaphthen-1-yl)piperidin-4-yl]-1,3-dihydro-2H-benzimidazol-2-one,
(R)-2-{3-[1-(acenaphthen-1-yl)piperidin-4-yl]-2,3-dihydro-2-oxo-benzimidazol-1-yl}-N-methylacetamide, and
(R)-1-[1-(acenaphthen-1-yl)piperidin-4-yl]-3-(2-oxo-2-piperazin-1-ylethyl)-1,3-dihydro-2H-benzimidazol-2-one.

In the present specification, (R)-2-{3-[1-(acenaphthen-1-yl)piperidin-4-yl]-2,3-dihydro-2-oxo-benzimidazol-1-yl}-N-methylacetamide is the most preferable compound.

The compound represented by the formula (I) can be synthesized according to the methods described in WO03/082333.

In the present specification, (R)-2-{3-[1-(acenaphthen-1-yl)piperidin-4-yl]-2,3-dihydro-2-oxo4enzimidazol-1-yl}-N-methylacetamide is sometimes to be also referred to as Compound A. As the pharmaceutically acceptable salt, acid addition salts with inorganic acid and organic acid can be mentioned.

The pharmaceutical agent of the present invention can be administered orally or non-orally. Dosage form includes tablet, capsule, granule, powder, injection, oral tablet, lotion, liniment, ointment, suppository and the like. These can be formulated by generally used techniques.

The amount of compound (I) or a pharmaceutically acceptable salt thereof, an active ingredient in these formulations, is 0.1 to 100% by weight, suitably 1 to 50% by weight. In addition, the dose may be suitably determined depending on symptoms, age, dosage form and the like. For the oral formulation, the dose is usually 0.1 to 5000 mg, preferably 1 to 1000 mg per day, and may be administered in a single dose or divided doses.

EXAMPLES

While Example and Experimental Examples are shown in the following, these Examples are given for better understanding of the present invention, and do not limit the scope of the present invention.

The pharmacological action of the pharmaceutical agent of the present invention is explained by way of 20 Experimental Examples.

Experimental Example 1

Effect on Alcohol Withdrawal Symptoms in Wistar Rats (Experimental Method)

Male Wistar rats were used in this study. According to the protocol shown in FIG. 1, rats were orally given 12-15 g/kg/body weight of ethanol in 24 hours on day 1 to day 2 and 9-10 g/kg/body weight of ethanol in 12 hours on day 3 to day 5. Compound A was administered p.o. at doses of 0.3 and 1 mg/kg/body weight twice after 2 and 7 hours of last ethanol administration. Four types of alcohol withdrawal symptoms such as vocalization, ventromedial limb retraction, tail rigidity, tail tremors were observed and scored with following 3 rating scales: mild=0, moderate=1, severe=2.

(Results)

Figure 2:
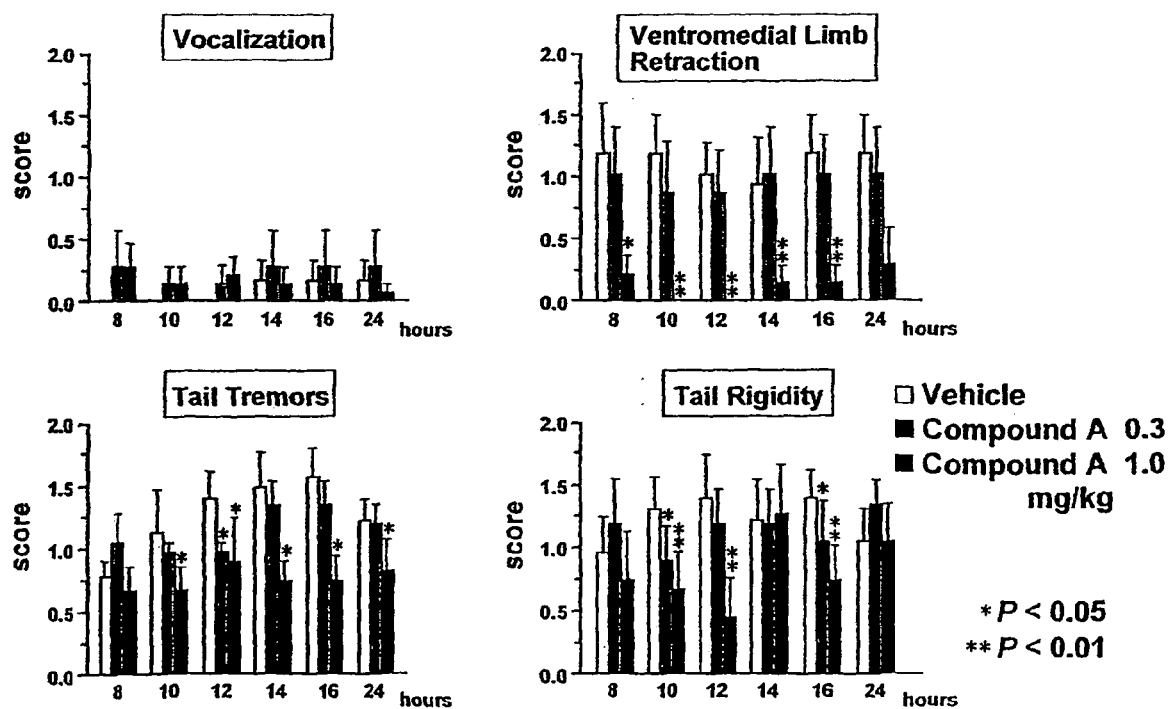
FIG. 2 shows the action of Compound A on alcohol withdrawal symptoms.

As shown in FIG. 2, 0.3 and 1 mg/kg/body weight of Compound A significantly and dose-dependently decreased scores of ventromedial limb retraction, tail rigidity and tail tremors, which were observed 8 to 24 hours after the last ethanol administration.

Experimental Example 2

Effect on Alcohol Intake in msP Rats (Experimental Method)

Figure 3:
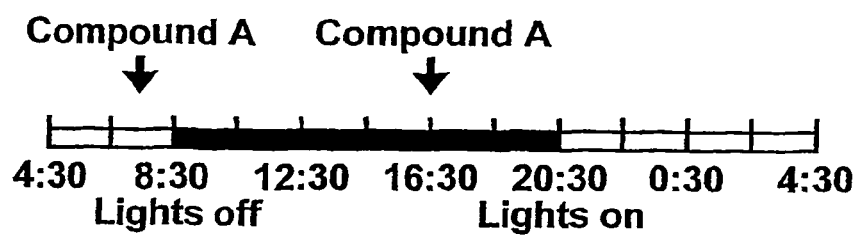
FIG. 3 shows a test protocol of ethanol intake measurement in msP rats.

Male genetically selected alcohol-preferring rats known as Marchigian Sardinian alcohol-preferring (msP) rats were used in this study (Addiction Biol. 11, 339-355, 2006). As shown in FIG. 3, the rats were housed in reverse light-dark condition (light off at 8:30, light on at 20:30) and ethanol consumption was measured everyday under free choice between water and 10% ethanol. Compound A at doses of 0.3 and 1 mg/kg/body weight was orally administered twice for 9 days at 1 hour before and 8 hours after onset of dark period.

(Results)

Figure 4:
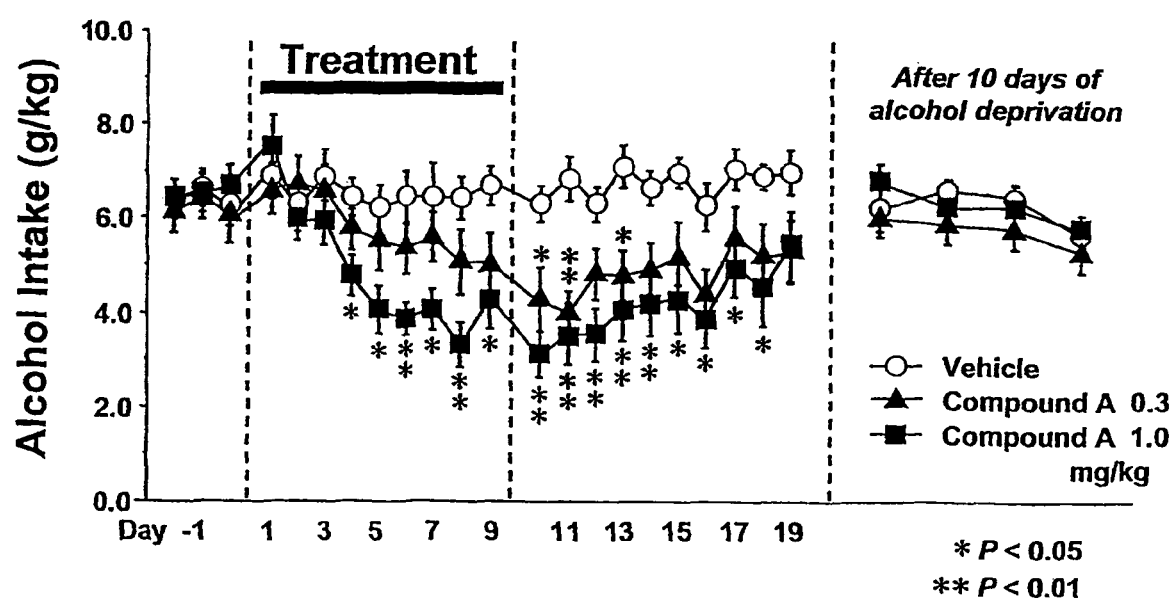
FIG. 4 shows the action of Compound A on the ethanol intake in msP rats.

As shown in FIG. 4, 0.3 and 1 mg/kg/body weight of Compound A significantly and dose-dependently decreased ethanol consumption in msP rats. This effect was long-lasting and significant for 9 days after withdrawal of Compound A.

Experimental Example 3

Figure 5:
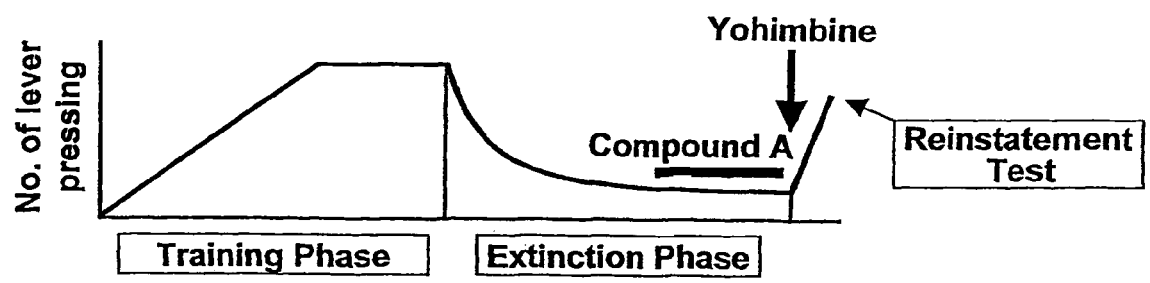
FIG. 5 shows a test protocol of yohimbine-induced reinstatement in msP rats.

Effect on Yohimbine-induced Reinstatement of Alcohol-seeking Behavior in msP Rats (Experimental Method)
Male genetically selected alcohol-preferring rats known as msP rats were used in this study (Addiction Biol. 11, 339-355, 2006). As shown in FIG. 5, rats were trained to self-administer 10% (w/v) ethanol in 30-min daily sessions under a fixed-ratio 1 (FR 1) schedule of reinforcement, where each response resulted in delivery of 0.1 ml fluid. After acquisition of a stable baseline of 10% ethanol self-administration, rats were subjected to 30-min extinction sessions for 15 consecutive days. Extinction sessions were identical to 10% ethanol self-administration sessions, however alcohol was no longer available. Beginning on extinction day 10, rats were divided into three groups with similar baseline levels of responding for 10% ethanol. For six consecutive days, 1 hour before the self-administration session and 8 hours later, each group of rats were orally given vehicle, 0.3 mg/kg of Compound A or 1.0 mg/kg of Compound A. After the extinction sessions, rats were given yohimbine (1,25 mg/kg, i.p.) 35 min before the test sessions. The 30-min reinstatement test was conducted under extinction condition.

Figure 6:
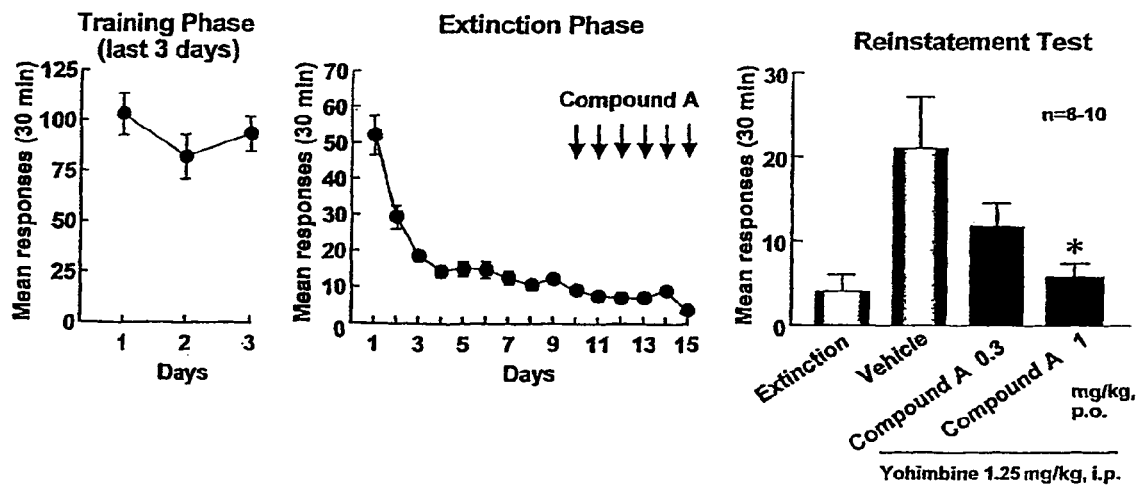
FIG. 6 shows the action of Compound A on yohimbine-induced reinstatement in msP rats.

Yohimbine was used as stressor for this study, because yohimbine is known to produce stress and anxiety-like states in both humans and non-humans (Bremner et al, 1996; Charney et al 1983; Holmberg et al 1963).
(Results)
As shown in FIG. 6, treatment with 1 mg/kg of Compound A significantly attenuated yohimbine stress-induced reinstatement of alcohol-seeking behavior.

Experimental Example 4

Figures 7, 8:
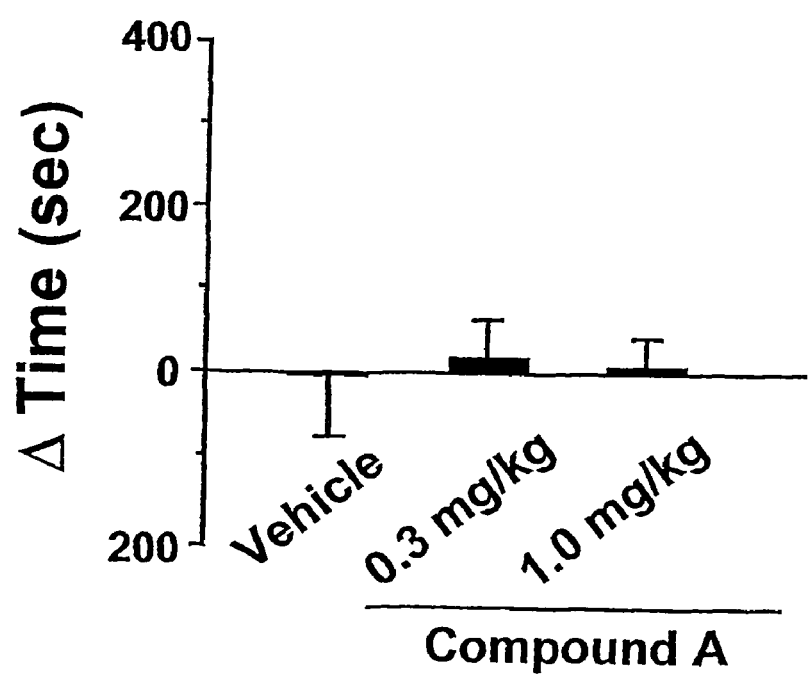
FIG. 7 shows a test protocol of the conditioned place preference in msP rats.
FIG. 8 shows the effect of Compound A on the place preference in msP rats.

Study on Dependence Elicitation in msP Rats (Experimental Method)
A two-compartment box divided by guillotine door was used. As shown in FIG. 7, in the first two days, rats were allowed to explore the box with guillotine door open for 15 min (pre-conditioning). For the following 6 days, the rats were treated on alternate days with three Compound A-pairing administrations (0.3 and 1.0 mg/kg/body weight, p.o.) and three vehicle-pairing administrations immediately before being placed, for 1 hour, into the assigned chamber with guillotine door close for drug-compartment discrimination (conditioning). The day after the last conditioning session, the rats were placed, for 15 min, in the box with door open. The time spent in the drug paired compartment was measured.
(Results)
As shown in FIG. 8, Compound A induced place preference at neither 0.3 nor 1 mg/kg/body weight, suggesting Compound A itself does not elicit dependence.

Comparison of pharmacological profiles between Compound A and existing medicines for alcohol dependence is summarized in Table 1. Although naltrexone and acamprosate (both have been marketed in Europe and USA) are effective in excessive alcohol intake, these medicines are ineffective in alcohol withdrawal symptoms and stress-induced reinstatement. Benzodiazepines represented by diazepam are used for a treatment of alcohol withdrawal symptoms, but it is known that benzodiazepines themselves have demerit to induce dependence.

Alpha-2 adrenergic agonists represented by clonidine are also effective in alcohol withdrawal symptoms (Dobrydnjov et al., Anesth Analg. 98, 738-744, 2004), but ineffective in excessive alcohol intake and stress-induced reinstatement.

On the other hand, Compound A has not only suppressive effect on excessive alcohol intake, but also ameliorative effect on alcohol withdrawal symptoms and suppressive effect on stress-induced reinstatement. Furthermore, Compound A itself does not elicit dependence. From these results, Compound A is expected to be a good agent for the prophylaxis or treatment of alcohol abuse and dependence and other substance abuse and dependence.

TABLE 1

|  | Ameliorative effect on alcohol withdrawal symptoms | Suppressive effect on excessive alcohol intake | Suppressive effect on stress-induced reinstatement | Presence/absence of dependence |
| --- | --- | --- | --- | --- |
| Naltrexone | none | yes | none | absent |
| Acamprosate | none | yes | none | absent |
| Diazepam | yes | none | none | present |
| Clonidine | yes | none | none | absent |
| Compound A | yes | yes | yes | absent |

Example 1

Formulation Example (Tablet)
The following ingredients were mixed according to a conventional method in a conventional apparatus and tableted.

| | |
| --- | --- |
| Compound A | 10 mg |
| microcrystalline cellulose | 180 mg |
| cornstarch | 300 mg |
| lactose | 600 mg |
| magnesium stearate | 15 mg |

Industrial Applicability

The pharmaceutical agent of the present invention can be used as an agent for the prophylaxis or treatment of substance abuse and dependence.

This application is based on EP patent application No. 06122336.8 filed on Oct. 16, 2006, the contents of which are incorporated in full herein by this reference.

The invention claimed is:
1. A method for the treatment of abuse of and dependence on alcohol, which comprises administering to a patient in need of such treatment an effective amount of (R)-2-{3-[1-(acenaphthen-1-yl)piperidin-4-yl]-2,3-dihydro-2-oxo-benzimidazol-1-yl}-N-methylacetamide,
or a pharmaceutically acceptable salt thereof.
2. The method of claim 1, wherein the treatment of abuse of and dependence on alcohol is for
 (i) amelioration of withdrawal symptoms; and
 (ii) suppression of excessive intake of alcohol.
3. The method of claim 1, wherein the treatment of abuse of and dependence on alcohol is for
 (i) amelioration of withdrawal symptoms;
 (ii) suppression of excessive intake of alcohol; and
 (iii) suppression of stress-induced reinstatement.

* * * * *